ns

PROCESS FOR INTEGRATED PRODUCTION OF ETHANOL AND SEAWEED SAP FROM KAPPAPHYCUS ALVEREZII

CROSS REFERENCE TO RELATED APPLICATIONS

This application is a U.S. National Stage application under 35 U.S.C. §371 of International Patent Application Serial No. PCT/IN2010/000508, filed Jul. 30, 2010 and Amended Under PCT Article 34 on Jul. 5, 2011 which claims the benefit of the Indian Patent Application No. 1839/DEL/2009, filed Sep. 7, 2009, the disclosures of each of which are expressly incorporated by reference in their entireties.

FIELD OF THE INVENTION

The present invention relates to an integrated process for the production of ethanol and seaweed sap from *Kappaphycus alvarezii*. More specifically, the invention relates to a process for producing ethanol from phycocolloid rich red seaweed, *Kappaphycus alvarezii*.

BACKGROUND OF THE INVENTION

Ethanol nowadays is an important product for its high demand in the fuel market. Its market grew from less than a billion liters in 1975 to more than 39 billion liters in 2006 and is expected to reach 100 billion liters in 2015 (Licht 2006). Global ethanol production is more than doubled between 2000 and 2005, while production of biodiesel, starting from a much smaller base, expanded nearly fourfold. By contrast, world's oil production is increased by only 7 percent during the same period. Less than 4% of ethanol is produced synthetically from petroleum, while the rest is produced by fermentation from bioresources. Ethanol is now produced from two major groups of bioresources: sugar substances and starchy materials. There is a competition between these two feedstock for fuel ethanol production. Sugar substances were the feedstock for more than 60% of fuel ethanol production at the beginning of the 2000s, its share decreased to 47% by 2006, when grains accounted for 53% of the production (Licht 2006, "World ethanol markets: The outlook to 2015," Tunbridge Wells, Agra Europe special report, UK).

The production and use of biofuels have entered a new era of global growth. The two primary biofuels in use today are ethanol and biodiesel. Ethanol is readily blended with gasoline, and biodiesel is blended with petroleum-based diesel for use in conventional diesel-fueled engines. Ethanol currently accounts for more than 90 percent of total biofuels production, with biodiesel making up the rest. Ethanol has a potential market as big as the oil market. It can potentially replace the entire fuel market for gasoline. Methanol or ethanol is also used for manufacture of biodiesel, during the process of transesterification.

Nearly, all fuel ethanol is produced by fermentation of corn sugar and sugarcane wastes. The amounts of sugar substances and grains are limited in the world and they are relatively expensive feedstocks for ethanol production. Bioethanol production using these substances results in competition with human food which may lead to increase in the price of grains and sugar to higher levels in the future. Ethanol-based biofuels are generally derived from fermenting the carbohydrates present in corn and soy, which are cheap to produce. However, cultivating these crops, require huge area of land that can displace acreage required for food.

Due to limited availability of agricultural land, it is essential that we do not ignore the potential of the marine environment as a source of biomass for ethanol production. It is known that macroalgae may be cultivated easily, grow prolifically and sequester carbon. In addition, the aquaculture of seaweeds reduces contribution to eutrophication of the seas and therefore may be used to mitigate the effects of sewage effluent and industrial sources of nitrogenous waste such as those originating from fish aquaculture, contributing to the maintenance or improvement of biodiversity.

Macro algae, more commonly known as "seaweeds", are diverse group of fast growing marine plants and occur as attached forms to rocks in both intertidal as well as shallow subtidal waters. These plants being autotrophic, use energy from the sun to combine water with carbon dioxide ($CO_2$) to produce carbohydrates and ultimately biomass. This biomass is harvested throughout the world as a food source as well as export materials for the production of phycocolloids. Seaweeds are cultivated commercially in several Asian countries such as China, Japan, Philippines and Korea since the demand for seaweeds and seaweed based products outstripped the supply from wild stocks. Further, the increase in demand started to spur research and development of culture methods as well as extraction processes for sustainable production and utilization of seaweed resources. These seaweeds can be grown on commercial scale in the sea where area is unlimited and huge biomass can be generated without precise agricultural practices.

These seaweeds can be used for biofuel production, specifically for bioethanol production as they are more appropriate for bioethanol production as compared to biodiesel production for following reasons.

1. Carbohydrate content of some of the seaweeds is very high.
2. The lipid (oil) content in seaweeds is less as compared to carbohydrate content which makes them less suitable for biodiesel production.
3. For ethanol production, dry/semidry or fresh seaweeds can be used. They do not require any pretreatment like drying.
4. Extraction of oil is required for biodiesel production, for which the material needs to be dried which is energy incentive.
5. $CO_2$ generated through ethanol fermentation can be used as algae feedstock.

Red algae are globally important seaweeds having high growth rate. They are representatives of diverse origin; more complex thalli are built up of filaments. The red algae *Kappaphycus* and *Betaphycus* are now the most important sources of carrageenan used in food industry. *Gracilaria, Gelidium, Pterocladia* and other red algae are used in the manufacture of agar, widely used as a gelling agent in growth medium for microorganisms and for biotechnological applications. These algal cell walls are made up of long chain polysaccharides like cellulose and agars/carrageenans having widespread commercial use.

Carrageenan is a family of linear sulphated polysaccharides extracted from red seaweeds of *Kappaphycus* and *Betaphycus*. Carrageenan is made up of sodium, potassium, magnesium and calcium sulfate esters of galactose and 3,6-anhydrogalactose units. Three basic types of carrageenan are available, which differ in the numbers and location of sulfated ester. These polysaccharides are large, highly flexible molecules, which curl around each other forming double helical structures in the presence of monovalent and divalent cations. This gives them the ability to form a variety of thermoreversible gels at room temperature. Carrageenan content varies from 25-35% on dry weight basis in different carrageenophytes. Carrageenan is widely used in the food and pharmaceutical industries as thickening, stabilizing and gelling agents.

Until recently, the seaweed industry in India had relied exclusively on harvesting of the natural stock. Primarily, this had focused on *Sargassum* (for alginates and liquid seaweed fertilizer), *Gracilaria edulis* (for low grade agar) and *Gelidiella acerosa* (for moderately superior grade agar). All this has undergone a dramatic change over the last five years. On the one hand, *Kappaphycus alvarezii* was adapted in Indian waters and its cultivation is demonstrated to be viable as a result of a decade long research (U.S. Pat. No. 6,858,430 dated Feb. 22, 2005). The technology was subsequently licensed by CSMCRI which, in turn, has spurred the cultivation activity in Tamil Nadu by self help groups and NGOs with buy back guarantee from the end user. Over the past twenty years, large-scale cultivation of carrageenophytes is successfully carried out all over the world including India and hence there is no shortage of carrageenan yielding seaweed. Given the fact that seaweeds contain water more than 90% on fresh weight basis, CSMCRI invented a unique process (U.S. Pat. No. 6,893,479) of liquefying the fresh seaweed without adding any water. Through this simple process, two products could be recovered in an integrated manner, one being a concentrated residue rich in •-carrageenan and the other being the plant sap (liquid seaweed fertilizer-LSF) rich in major and minor plant nutrients. To fulfill the demand of agriculture, massive biomass of *Kappaphycus alvarezii* is required which can be achieved through on shore and off-shore cultivation. After recovery of sap, large amount of residual biomass rich in carrageenan will be generated. Once raw material requirement for k-carrageenan is satisfied, the residual biomass can be used for bioethanol production. Thus, recovery of multiple products from seaweed would make cultivation economically more viable. Good cultivation practices may prove *Kappaphycus*, a cheaper raw material, for ethanol production. These developments are of vital importance from the perspective of massive expansion of the seaweed based industries while at the same time focusing on sustainability.

A major criticism often faced against large-scale fuel production using food crop's, is that it could divert agricultural production away from food crops, especially in developing countries. The fact is that energy-crop programmes compete with food crops with respect to use of agricultural land, water, fertilizers, skilled labour etc. which leads to increase in food price. Also, cultivation of crops for biofuel production will have impacts on biological diversity. Hence there is an urgent need to identify an alternative source for bioethanol production which overcomes all the limitations. Marine algae/seaweeds is the ideal option as they grow in the sea, where vast area for cultivation is available and due to high growth rate, generates huge biomass without special agricultural practices, thus, reducing the pressure on agricultural land. Apart from these, they are rich in carbohydrates and hence ideal source for bioethanol production.

PRIOR ART

Reference may be made to U.S. Pat. No. 6,893,479 (2007) assigned to Eswaran et al entitled "Integrated method for production of carrageenan and liquid fertilizer from fresh seaweeds" have disclosed an integrated method to obtain multiple products from fresh biomass of *Kappaphycus alvarezii* and thereby enhanced the value of the seaweed. These products are i). sap, a potential liquid biofertilizer and ii). a granular carrageenan rich residual material. This residual material is the raw material for extraction of k-carrageenan. The drawback of the patent is utilizing the residual material only for one product i.e. k-carrageenan preparation. No mention is made on utilization of carrageenan rich granular material for the production of ethanol.

Reference may be made to Maleszka et al in their paper entitled "Ethanol production from D-galactose and glycerol by *Pachysolen tannophilus*" in Enzyme and Microbial Tech. (1982) 4(5): 349-352 have described the production of ethanol from previously considered nonfermentable sugars like D-galactose and glycerol. They studied ethanol production from monosaccharides like D-galactose, D-glucose, D-mannose or D-xylose or glycerol. They reported that *Pachysolen tannophilus* converted all the major plant monosaccharides, mentioned above, to ethanol. They also stated that the same yeast have the ability to ferment glycerol derived from algae into ethanol. The drawback of this paper is use of plant monosaccharide as substrates for ethanol production. No mention has been made about the use marine algae or marine algal polysaccharides for ethanol production.

Reference may be made to U.S. Pat. No. 5,270,175 (1993) assigned to M Benjamin entitled "Methods and compositions for producing metabolic products for algae", has disclosed the transformation and use of transformed marine macro algal cells for the production of ethanol. They selected *Enteromorpha* sp. based on its rapid growth and ability to form a dense mat in the growth pond within two months. They prepared protoplasts from *Enteromorpha* and modified the algal cells by inserting alcohol dehydrogenase gene and/or pyruvate decarboxylase under the control of high expression promoter gene. They cultured alcohol-producing transformants in 200 ml seawater medium and flooded the cultures with seawater every 2-3 days for five to seven times in shallow ponds. They reported that overexpression of at least one enzyme in the metabolic pathway of algal cells resulted in production of metabolic products. The draw backs of this patent are a) used genetically modified seaweed where starch is the major polysaccharide b) genetic transformation is a complicated process and requires continuous monitoring c) due to transgenic nature of the plant, it has to clear regulatory norms before its use. No mention has been made about the use *Kappaphycus alvarezii* for ethanol production. Also ethanol is not produced as a by product.

Reference may be made to U.S. Pat. No. 5,578,472 (1996) assigned to Ueda et al entitled "Process for the production of ethanol from microalgae" have disclosed the process for the production of ethanol from microalgae. They cultured *Chlamydomonas reinhardtii* UTEX2247 capable of accumulating starch in the cells, harvested the algal cells, concentrated the algal culture solution containing the grown algal cells to obtain algal cell slurry and maintained the concentrated algal cells in slurry in dark and anaerobic atmosphere to form ethanol at pH in the range of 6.0 to 9.0. They subjected the residual slurry for methane fermentation, burning it to generate carbon dioxide, which was used in the microalgae culturing step. The drawbacks are a) use of microalgae b) starch, accumulated in algal cells, was a substrate for ethanol production c) fermentation process was undertaken under dark condition. No mention is made on using macroalgal polysaccharides (phycocolloids) as substrates for ethanol production.

Reference may be made to Hirano et al in their paper entitled "$CO_2$ fixation and ethanol production with microalgal photosynthesis and intracellular anaerobic fermentation" in Energy (1997) 22: 137-142 have examined ethanol productivity of microalgae. After isolating more than 200 microalgal strains from seawater and screening them for their growth rate, starch content and ethanol productivity, *Chlorella vulgaris* (IAM C-534) was identified as the most promising one with respect to starch content i.e. 37%. They extracted starch from the cells of the *Chlorella*, saccharified the starch, fermented with yeasts and obtained 65% of the ethanol conversion. They also examined another type of ethanol production process, i.e. intracellular starch fermentation under dark and anaerobic conditions. They reported that all of the tested strains showed intracellular starch degradation and ethanol production. Finally, they concluded that intracellular ethanol production is simpler and energy intensive than the conventional ethanol fermentation process. The drawbacks of this paper are a) use of microalgae b) use of extracted microalgal component, starch, as a substrate c) used intracellular starch fermentation under dark and anaerobic conditions. No mention is made on the use of the seaweeds or carrageenan rich material obtained from seaweeds as a substrate for the ethanol production.

Reference may be made to Ueno et al in their paper entitled "Ethanol production by Dark Fermentation in the Marine Green alga, *Chlorococcum littorale*" in J. of Fermentation and Bioengineering (1998) 86(1): 38-43 have studied dark fermentation in marine green alga, *Chlorococcum littorale* with emphasis on ethanol production. They reported that 27% of cellular starch was consumed within 24 h at 25° C. under dark anaerobic conditions through which, ethanol, acetate, hydrogen and carbon dioxide were produced as fermentation products. They have achieved the maximum ethanol productivity of 450 micromole/g-dry wt at 30° C. The drawback of this paper is a) use of microalgae having starch as carbohydrate c) fermentation process was undertaken in dark under anaerobic condition for ethanol production. They did not use macroalgae, particularly red seaweeds. Also no mention is made on use of yeast or bacteria for fermentation.

Hirayama et al in their paper entitled "Ethanol production from carbon dioxide by fermentative microalgae" in Studies in Surface Science and Catalysis (1998) 114: 657-660, have described ethanol production from fermentative microalgae fixing carbon dioxide. They screened more than 200 microalgal strains from seawater for $CO_2$ fixation and ethanol production by self-fermentation. The isolates were also tested for their growth rate, starch content, and conversion rate from starch to ethanol. They selected one of the excellent strains, *Chlamydomonas* sp. YA-SH-1 based on its higher growth rate (30 g-dry biomass/$m^2$.d), starch content (30% based on dry wt) and higher conversion rate from intracellular starch to ethanol (50%) in the dark and anaerobic condition. They cultivated *Chlamydomonas* sp., harvested and allowed for self-fermentation. Finally, they extracted ethanol from the fermentation broth. The drawback of this paper is a) use of microalga having higher starch content, b) used self-fermentation method under dark condition. No mention is made on the use of macroalgae particularly red seaweeds, having polysaccharides other than starch, for ethanol production and did not produce ethanol as a by product.

Reference may be made to Svein Jarle Horn, for his Ph.D thesis entitled "Bioenergy from brown seaweeds" submitted to Department of Biotechnology, Norwegian University of Science and Technology (NTNU), Trondheim, Norway in 2000, carried out research on using *Laminaria hyperborea* and *Ascophyllum nodosum* for energy production. In this work, laminaran and mannitol extracted from *L. hyperborea* fronds were used as substrate for ethanol production. He used *Zymobacter palmae* for ethanol production from mannitol, which could not utilize laminaran. However, the yeast *Pichia angophorae* was able to produce ethanol from both the substrates simultaneously. Finally, he has produced methane and ethanol from brown seaweeds. According to him, energy production from seaweeds would be economical if the harvesting costs are low. It may be noted that wastes from the alginate industry may be considered as a non-cost raw material for energy production. The drawback of this work is used brown seaweed. No mention is made on the use of red algae as a source of ethanol and production of ethanol as a byproduct.

Reference may be made to Horn et al in their paper entitled "Ethanol production from seaweed extract" in J. of Industrial Microbiology and Biotechnology (2000) 25: 249-254, have reported production of ethanol from brown seaweed extract. They prepared aqueous extract from fresh fronds of cultivated *Laminaria hyperborea* at pH 2.0 at 60° C. for 1 h. The extract contained mannitol and laminaran with the yield of 2% based on fresh weight. Four microorganisms, one bacterium and three yeasts, were used for fermentation in batch and continuous cultures. They achieved ethanol yield of 0.43 g/g substrate in batch culture. The drawback of this paper a) sacrificing whole plant of brown alga, *Laminaria hyperborea* and b) use of seaweed extract consisted of mannitol and laminaran as a sugar substrate. They did not use red algae for the ethanol production. Also, no mention is made on the production of ethanol as a byproduct.

Reference may be made to Matsumoto et al in their paper entitled "Saccharification of marine microalgal biomass for bioethanol production using marine bacteria" in Appl. Biochemistry and Biotechnology (2003) 105: 247-254, have reported the method of saccharification of marine microalgal polysaccharide using marine bacteria. Out of 191 strains of marine bacteria isolated, *Pseudoalterimonas undina*, was identified, as the most potential bacterial culture with respect to saccharification under saline condition. A green microalga NKG 12070, having highest concentration of intracellular carbohydrate such as starch was used. After inoculating *Pseudoalterimonas undina* into algal cells suspension, due to amylase production, increase in reducing sugar concentration was observed. The drawbacks are a) use of microalgae as a raw material where starch is the major carbohydrate b) they used enzymatic process for saccharification. No mention is made for use of seaweeds for ethanol production.

Reference may be made to U.S. Pat. No. 6,699,696 (2004) assigned to Woods et al entitled "Genetically modified cyanobacteria for the production of ethanol, the constructs and method thereof" have disclosed the method of ethanol production from genetically modified cyanobacteria particularly *Synechococcus*. They constructed DNA fragments encoding pyruvate decarboxylase and alcohol dehydrogenase enzymes obtained from the *Zymomonas mobilis* in pLOI295 plasmid. These two enzymes are required for production of ethanol from pyruvate, a product of glycolytic pathway. The harvested cyanobacterial cells were modified by incorporating the constructs and inoculated on ampicillin containing plates for the selection of the transformed ampicillin resistant cyanobacterial cells. These modified *Synechococcus* cells were capable to produce ethanol in a recoverable quantity of at least 1.7 μmol ethanol per mg of chlorophyll per hour. The drawback of this patent is a) use of micro algae, particularly genetically modified *Synechococcus* which requires precise expertise and continuous monitoring. No mention is made on the use of seaweeds for the production of alcohol.

Reference may be made to U.S. Pat. No. 7,135,308 (2006) assigned to Bush et al entitled "Process for the production of ethanol from algae" have disclosed a process for the production of ethanol by harvesting starch-accumulating, filament-forming or colony-forming algae from natural water sites to form a biomass, initiating cellular decay, fermenting and isolating ethanol from fermented broth. They kept algal biomass in dark and anaerobic condition for initiating the decay of biomass followed by inoculation of yeasts like *Saccharomyces cerevisiae* and *Saccharomyces uvarum* to form a fermentation solution from which generated ethanol was separated. The drawbacks of the patent are a) use of mixed algal culture as they used natural micro algal blooms b) used algal component, starch as a substrate. They did not use pure culture of microalgae since experiments were conducted with algal blooms. No mention is made on a) the hydrolysis of starch in to simple sugars before fermentation and b) use of macroalge for ethanol production and ethanol is not produced as an additional product.

Reference may be made to Jessica et al (2008) in their paper entitled "Fermentation study on *Saccharina latissima* for bioethanol production considering variable pretreatments" published in Journal of Applied Phycology (DOI 10.1007/s10811-008-9384-7) described the effect of enzymatic pretreatment of alga on bioethanol production using a brown alga *Saccharina latissima* (*Laminaria saccharina*). Laminarin and mannitol are the major carbohydrates obtained from pheophyta apart from alginic acid. Amount of all the three carbohydrates varies with season and life cycle of the plants. Laminarin consists of $\beta$-1,3-linked glucose residues with small amount of $\beta$-1,6-linkages. This polysaccharide is easily hydrolyzed with laminarinase under different pH and temperature conditions. However, maximum ethanol production (0.49%) was obtained with the sample treated with enzyme at pH 6 at 23° C. The drawback of the paper is a) sacrificing whole seaweed b) generation of high salt content in the hydrolyzate during pretreatment due to pH adjustment which hinders ethanol production c) ethanol is not produced as an additional product.

Reference may be made to Researchers from Tokyo University of Marine Sciences and Technology, Mitsubishi Research Institute, (available at pinktentacle.com/2007/03/seaweed-as-biofuel), March 2007, released details of an ambitious proposal of large scale production of bioethanol from cultivated seaweed. According to them, seaweed has long been discussed as a potential source of bioethanol which is typically made from crops such as sugar cane and corn, but idea has never been brought to reality. According to them, sargasso seaweed will be cultivated on large scale due to its higher growth rate followed by enzymatic sachharification of algal polysacchaides like fucoidan and alginic acid and subsequently fermentation for the production of ethanol. According to them, apart from production of ethanol, the seaweed would help to clean up the sea of japan by reducing excess nutrients present in the sea. The drawbacks of the proposals are 1. Use of brown algae for ethanol production 2. sacrificing whole seaweed for ethanol production 3. replacing cultivation of food algae like nori and wakame with brown algae *Sargassum* 4. Applying enzymatic saccharification process which is relatively slow. They did not mention use of red algae and no mention is made on production of ethanol as a byproduct.

Reference may be made to the professional Journal engineer in his article entitled "Denmark looks to turn a common seaweed into biofuel" (available at www.ambathen.um.dk/da/menu/OmOs/Klimaforandringer/DENMARKLOOKS TOTURNACOMMONSEAWEEDINTOBIOFUEL. htm?WBCMODE=Pre %2CPresentationU) dated Jan. 7, 2008 mentioned of funding a project to assess the potential of producing bioethanol from sea lettuce (seaweed). He has mentioned that a green alga, *Ulva lactuca*, has the potential for bioethanol production. He pointed out the observation of michael bo rasmussen of the national environmental research institute at the university of aarhus where he mentioned sea lettuce as a rich potential resource for making bioethanol from a non-food biomass resource rather than from cereal crops such as corn and maize.

Reference may be made to Hiroshi Yamazaki, in his article entitled "Japan experiments with new biofuels" (avalable at bioenergy.checkbiotech.org/news/2007-06-27/japan_experiments_with_new_biofuels/) dated Jun. 1, 2008 reported that Japanese companies have begun introducing bioethanol fuel to the market in hopes of significantly reducing $CO_2$ emissions. He also added that the domestic production of the biofuel, particularly out, of edible materials, appears to be a distant goal. Nonetheless, promising experimentation with new materials, including seaweed and scrap wood, is attracting attention.

Recently an article available at www.eurozone-invest.com/biofuel.html describes Use of seaweed or algae for the production of bioethanol and biodiesel. According to this, cultivating algae for biodiesel production is more difficult as they require specific environment to be highly productive and can get easily contaminated by undesirable species. On the other hand, seaweeds and algae are rich in complex sugars like starch, amount of which is higher than oil present. This polysaccharide, through conversion and fermentation, turned into ethanol.

Reference may be made to Aizawa et al in their paper entitled "Seaweed Bioethanol Production in Japan—The Ocean Sunrise Project" in Oceans 2007 stated that the project aims to produce seaweed bioethanol by farming and harvesting *Sargassum horneri*, utilizing 4.47 million $km^2$ (sixth largest in the world) of unused areas of the exclusive economic zone (EEZ) and maritime belts of Japan. They also added that through seaweed bioethanol production, the project aims to combat global warming by contributing an alternative energy to fossil fuel. This paper outlines the results of the project's feasibility research conducted by Tokyo Fisheries Promotion. The drawback of this paper is a) use of *Sargassum horneri* for ethanol production. They did not carry out ethanol production and no mention is made on the extraction of galactose from red algal intracellular compound.

Recent report entitled "seaweed biofuel developed" available at www.prensa-latinaenglish.com/article.asp?id=%7B6392ED95-9842-486E-¥B4E5-676A4FA23D61%7D)&language=en dated Jun. 2, 2008 describes that biofuel prepared from seaweeds might be in alternative for ethanol, which obtained from food crops which is associated to the rise in food prices. In this article, Bernard Stroazzo, (president of Bio Fuel-System) stated that biofuel production from seaweed is promising and the product would neither affect the environment nor the feeding the population would be at risk. According to him, the seaweeds have very efficient photosynthesis system recovering 100% of the solar energy compared to other biofuels. However, the greatest problem lies with researchers in identifying suitable seaweed species from which generation of high amount of biofuels is possible.

Rricardo Radulovich in his article entitled "let's use seaweed as fuel" in COSMOS magazine (available at www.cosmosmagazine.com/node/2040) dated Jun. 10, 2008 mentioned that seaweed is generally used as food, fertilizer and animal feed but can also be used as a major fuel. He also stated the advantages of using seaweeds for biofuel production like no requirement of soil and water.

Algenol, a privately owned company, is engaged in broad research and development efforts to develop industrial-scale production systems to make ethanol from algae on desert land using seawater and large amounts of $CO_2$. Algenol uses cyanobacteria (blue green algae) by natural selection, environmental selection, and the tools of molecular biology to produce low cost and environmentally safe biofuels. Like all plants, algae uses photosynthesis to convert solar energy into chemical energy stored in the form of oils, carbohydrates and proteins. Algenol's patented technology produces ethanol from four abundant and virtually limitless renewable sources: Algae, sunlight, carbon dioxide and seawater. The outputs from this process are ethanol, oxygen, freshwater and agricultural fertilizer. Algenol's process has a large positive energy balance and does not require planting, harvesting, feedstock transportation, fossil fuel-based fertilizers and does not release $CO_2$ during the growing or ethanol production process. The company believes that its seawater-based process can generate 6,000 gallons per acre per year, in contrast to corn and sugarcane which yield approximately 360 and 890 gallons per acre respectively. During the process, an alga consumes sunlight and more than 90 percent of the system's co.sub.2 through photosynthesis, wherein the sugars are converted into ethanol. The ethanol is immediately pumped out and evaporates into the bioreactor which is captured every night. The drawback of the invention is utilization of blue green algae and not seaweeds. Also no mention is made on production of ethanol as a byproduct.

KBS World Radio published a report entitled "Researchers produce bioethanol with seaweed" on Jun. 17, 2008. According to this, The Korean Ocean Research and Development Institute said that researchers from the institute and Gangwon National University jointly produced bioethanol using a type of seaweed found on the coast of Jeju Island. The institute plans to push for follow up research to commercialize the technology.

According to a report published on 23 Jun. 2008, available at dsc.discovery.com/news/2008/06/23/ireland-seaweed-ethanol.html dated june 23, citing discovery news as, "seaweed power: ireland taps new energy source", Stephan Khan, head of Irish Seaweed Center at the National University of Ireland in Galway, an irish scientist, describes that ireland could become a key player in the production of biofuel from seaweed. According to him, algae do not have the negative image of terrestrial biomass resources, which are said to be responsible for higher food prices, impacting on water use and destruction of rain forests. International society for Applied Phycology is examining the economic and social aspects of using brown seaweeds for bioethanol production.

Ray Ryan, agribusiness correspondent wrote an article entitled as "Seaweed offers bright future for biofuel industry" published in the website of www.examiner.ie/story/business/gbojqlcwoj/rss2/dated Jun. 24, 2008. With reference to above, he told that with its rich, sustainable seaweed resources, ireland is poised to become an important player in the next generation of biofuel production.

Seaweedireland.com has published an article on Bio-fuel, bio-gas, electricity and heat available at dezeewierwinkel.nl/bio-fuel.html which describes that seaweed can be broken down by small micro-organism to produce different types of alcohol.

OBJECTIVES OF THE INVENTION

The main object of the present invention is to provide a process for integrated production of seaweed sap and ethanol from *Kappaphycus alvarezii* which obviates the drawbacks as detailed above.

Another object of the present invention is to provide a process for producing bioethanol from red seaweeds as a byproduct.

Yet another object of the present invention is to provide a process for producing bioethanol from red seaweeds, particularly from carrageenophytes.

Yet another object of the present invention is to produce bioethanol from carrageenophytes, particularly *Kappaphycus alvarezii*.

Still another object of the present invention is to produce bioethanol from carrageenan rich granules, generated from fresh *Kappaphycus alvarezii* after crushing and recovery of seaweed sap.

Still another object of the present invention is use of dilute sulfuric acid and elevated temperature for seaweed hydrolysis for conversion of seaweed polysaccharide to simple sugar.

Still another object of the present invention is increasing the sugar concentration up to 10% by repeatedly adding the fresh algal biomass to the hydrolysate.

Still another object of the present invention is to use solid calcium hydroxide for the neutralization of sulfuric acid of the sugar solution.

Still another object of the present invention is removal of insoluble $CaSO_4$ by filtration or centrifugation.

Still another object of the present invention is removal of soluble salts of the sugar solution by electrodialysis (ED).

Still another object of the present invention is enrichment of the hydrolysate with nitrogen sources like peptone, yeast extract or protein hydrolysate of *Jatropha* cake before sterilization.

Still another object of the present invention is inoculation of the brewer's yeast i.e *Saccharomyces cerevisiae*, culture No. NCIM 3455 (ATCC 26602) in the sterilized sugar solution.

Still another object of the present invention is fermentation of the sugar solution to ethanol.

Still another object of the present invention is separation of bioethanol from fermented broth by distillation as well as concentration of bioethanol.

Still another object of the present invention is utilization of residual matter after distillation of ethanol, in combination with $CaSO_4$ generated during neutralization and reject of ED process containing $K_2SO_4$ as the major soluble salt, as manure.

SUMMARY OF THE INVENTION

Accordingly, the present invention provides a integrated process for production of ethanol and seaweed sap from *Kappaphycus alvarezii*, the said process comprising the following steps:
(a) harvesting the cultivated red seaweeds from the Sea;
(b) extracting the sap from fresh *Kappaphycus* to release the liquid plant nutrient leaving carrageenan rich residual granular material;
(c) washing the residual granules to remove salt and silt;
(d) hydrolyzing the polysaccharide rich granules using dilute sulfuric acid in the range of 0.5-5% and heating the solution in the range of 80-200° C. for 30-90 minutes to obtain reducing sugar rich hydrolysate;
(e) recovering the solution by filtration or centrifugation in the range of 5000-7000 rpm for 15 minutes;
(f) increasing the sugar concentration in the hydrolysate by adding the fresh *Kappaphycus alvarezii* granules to the filtered solution and repeat the step (d) and (e) till sugar concentration is in the range of 2 to 10%;

(g) adjusting the pH of the hydrolysate in the range of 4.5 to 8.0 with alkali like calcium hydroxide, sodium hydroxide, calcium carbonate and potassium hydroxide;

(h) Separating insoluble salts by filtration or centrifugation in the range of 5000-7000 rpm for 15 minutes;

(i) desalting the hydrolysate, to remove soluble salts, by electro-dialysis;

(j) enriching the hydrolysate with nitrogen sources like peptone, yeast extract and protein hydrolysate of *Jatropha* cake in the range of 0.2-2.0% and then sterilizing it at 121° C. for 15 minutes;

(k) inoculating *Saccharomyces cerevisiae*, culture No. NCIM 3455 (ATCC 26602) to the enriched hydrolysate and incubating at 25-35° C. for a period in the range of 24 to 95 h;

(l) monitoring the ethanol production;

(m) separating ethanol from fermented broth by distillation;

(n) concentrating ethanol by distillation.

In an embodiment of the present invention, the carrageenan producing macro algae belonging to class Rhodophyta and the genus *Kappaphycus* is used for ethanol production where apart from seaweed sap, ethanol is produced as an additional product from carrageen rich granules.

In yet another embodiment of the present invention, the saccharification step comprises of acid hydrolysis of carrageenan rich granules at elevated temperature, wherein the polysaccharide is partially hydrolyzed to simple sugars such as galactose by dilute sulfuric acid in the range of 0.5% to 5.0% at temperature in the range of 80 to 200° C. for a period in the range of 30-90 min.

In yet another embodiment of the present invention, the reducing sugar concentration of the final hydrolysate is increased from 2.0% to 10% by repeated hydrolysis of fresh granules in the same solution.

In yet another embodiment of the present invention, the sugar solution is maintained in the range of 2% to 10%

In yet another embodiment of the present invention, the recovered sugar solution has pH in the range of 0.6 to 1.0.

In yet another embodiment of the present invention, the insoluble $CaSO_4$ generated during neutralization process is removed by filtration under vacuum or centrifugation at 7000 rpm for 15 minutes, whereas soluble salts are removed by electrodialysis method.

In yet another embodiment of the present invention, the hydrolysate is enriched with nitrogen sources like peptone and yeast extract or protein hydrolysate of *Jatropha* cake at the concentration in the range of 0.2-2.0%.

In yet another embodiment of the present invention, the active culture of standard brewers yeast i.e *Saccharomyces cerevisiae* culture No. NCIM 3455 (ATCC 26602) is inoculated in the autoclaved hydrolysate.

In yet another embodiment of the present invention, the inoculated seaweed hydrolysate is incubated in the range of 25-35° C. for a period in the range of 24 to 96 h under the aerobic and anaerobic conditions for fermentation of sugar to ethanol.

In yet another embodiment of the present invention, the bioethanol is separated from the fermented broth by distillation.

In yet another embodiment of the present invention, remaining fermented broth after distillation, in combination with insoluble $CaSO_4$ generated during neutralization and reject of electrodialysis process, are used as manure.

In yet another embodiment of the present invention, the final hydrolysate contains galactose as monosaccharide, partially hydrolysed oligosaccharides and unhydrolysed carrageenan.

In yet another embodiment of the present invention, calcium hydroxide is used to adjust pH of the hydrolysate in the range of 4.5 to 8.0.

In yet another embodiment of the present invention, the precipitated calcium sulphate removed either by filtration or centrifugation.

In yet another embodiment of the present invention, the hydrolysate is desalted to remove soluble salts using electrodialysis method In yet another embodiment of the present invention, the final hydrolysate is enriched with peptone and yeast extracts or protein hydrolysate of *Jatropha* cake to provide nitrogen source to fermenting organisms.

In yet another embodiment of the present invention, *Saccharomyces cerevisiae* culture No. NCIM 3455 (ATCC 26602) is inoculated to fermentation broth and incubated at 30° C. initially under aerobic and then under anaerobic condition for a period ranging from 24-96 hrs.

In yet another embodiment of the present invention, ethanol production during fermentation is monitored by GC-MS.

In yet another embodiment of the present invention, ethanol is concentrated and distilled from fermentation broth.

DETAILED DESCRIPTION OF THE INVENTION

Figure 1:
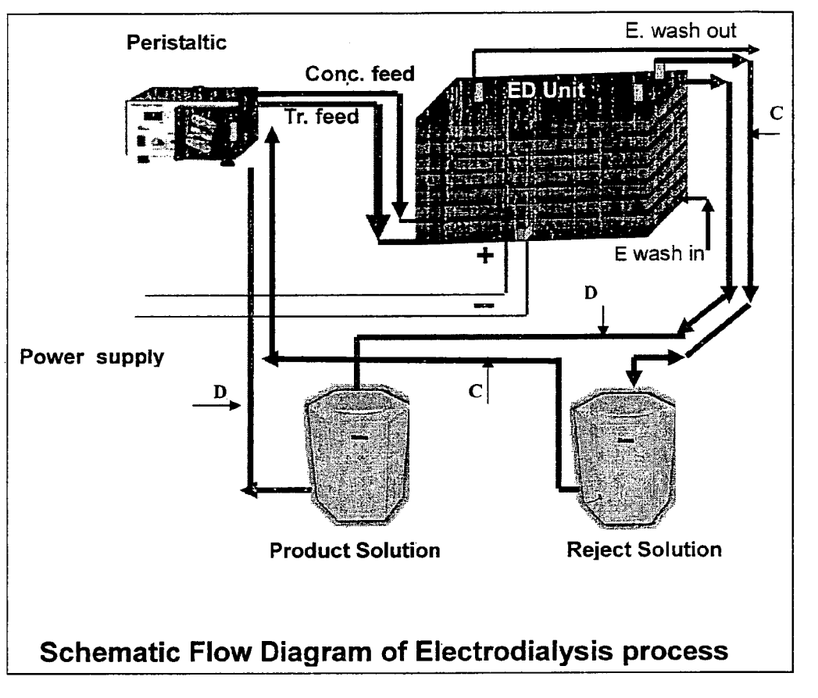
FIG. 1 The schematic flow diagram of the electrodialysis process.

The aim of the present invention is to produce bioethanol and more specifically is to provide a process for producing ethanol by the fermentation of macroalgal biomass. The present invention relates to the development of a process for the production of bioethanol using red algae by utilizing red algal phycocolloids as the source material. In the present invention, for the first time, bioethanol is produced from red seaweeds, particularly, *Kappaphycus alvarezii* as a byproduct. Red seaweeds are fast growing marine plants that composed of degradable polysaccharides, mainly either agar or carrageenan.

The process of bioethanol is generally comprised of saccharification and fermentation. Saccharification is usually done by concentrated/dilute acid hydrolysis and enzymatic hydrolysis followed by fermentation using either bacteria or yeasts. Saccharification is performed by subjecting algal biomass to dilute acid hydrolysis using sulfuric acid in the range of 0.5% to 5.0% at temperature in the range of 80-200° C. for a period in the range of 30-90 minutes. This has resulted in conversion of carrageenan to galactose with simultaneous generation of soluble salts due to high sulfate content of carrageenan. The reducing sugar concentration of recovered hydrolysate is increased by treating fresh biomass in the same solution under similar conditions. This process is repeated 3 to 5 times to achieve desired reducing sugar concentration in the range of 2 to 10% which is monitored spectrophotometrically using Nelson method. Increase in sugar concentration resulted in increase in concentration of soluble salt in the final hydrolysate. The pH of the resultant filtrate is adjusted in the range of 4.5 to 8.0 using calcium hydroxide.

Insoluble calcium sulfate precipitates, generated during the process of neutralization, are removed by filtration or centrifugation in the range of 5000-7000 rpm for 15 mins whereas soluble salts were removed by electrodialysis method. In this process, an electrodialysis stack was packed with 5 cell pairs of cation and anion exchange membranes of inter polymer type prepared in this laboratory. A parallel flow was employed in the stack. The single effective membrane area of the stack was 80 cm². The seaweed hydrolysate was circulated through the product (diluate) compartments of the ED stack. At the same time water was circulated through the concentrate compartments. All the experiments were carried out with circulation flow rate of 3.0 L/h each for product and concentrate streams by using suitable pumps. A dilute solution of sodium sulfate was circulated through the two electrode compartments at the end to flush out the products of electrodialysis. Electrical potential (7.5 V) was applied between the two electrodes by means of an AC-DC rectifier. The circulation of both diluate and concentrate streams were continued till the total dissolved salt rejection reaches about 90-95% of the initial quantity. At regular intervals current, voltage and TDS were recorded. At the end of the experiment, test samples of diluate and concentrate streams were analyzed for TDS, conductivity, pH, chloride, sulfate, hardness, sodium, potassium etc.

After electrodialysis process, the final hydrolysate, containing monosaccharide, partially hydrolysed oligosaccharides or unhydrolysed polysaccharides is enriched with nitrogen sources like peptone, yeast extract or protein hydrolysate of *Jatropha* cake in the range of 0.2 to 2.0%, autoclaved and subjected to fermentation by inoculating with *Saccharomyces cerevisiae* culture No. NCIM 3455 (ATCC 26602) and incubating it at 25-35° C. for a period in the range of 24 to 96 hours to convert its simple sugar to ethanol. Ethanol production is monitored at regular interval using GC-MS (Shimadzu GC: 2010) coupled with GC-MS (QP 2010) through head space (AOC-5000) analyzer where as reducing sugar of the fermented solution is measured to determine the fermentation efficiency. Finally, generated ethanol is separated from the fermented broth by distillation and residual material is used as manure Bioethanol is recovered from the fermented broth by distillation, though recovered ethanol is not of fuel grade, can be converted to fuel grade by concentrating it via methods like distillation, membrane purification, chemical drying, or combination of methods.

Finally, the present invention describes bioethanol production as a byproduct using galactose of red seaweeds.

The inventive steps adopted in the present invention are i) developing an integrated process for producing seaweed sap and ethanol from red seaweed generating ethanol as a by product iii) using red seaweed as a raw material for ethanol production iv) using sulfated polysaccharides of carrageenan rich raw material of red seaweed as a source of ethanol v) hydrolyzing the carrageenan rich raw material with sulfuric acid for conversion of polysaccharide to monosaccharides vi) increasing the sugar concentration of the hydrolysate by repeated hydrolysis of fresh granules in the same solution vii) using calcium hydroxide for neutralization viii) removing generated insoluble $CaSO_4$ by filtration or centrifugation ix) desalting soluble salts from the hydrolysate by electrodialysis process ix) enriching the hydrolysate with nitrogen sources x) fermenting the broth with actively grown yeast culture of *Saccharomyces cerevisiae*, culture No. NCIM 3455 (ATCC 26602) xi) recovering ethanol by distillation and xii) using reject of electrodialysis, containing potassium sulfate and sodium sulfate as fertilizer, in combination with $CaSO_4$ generated during neutralization and residual material after ethanol distillation.

EXAMPLES

The following examples are given by way of illustration and therefore should not be construed to limit the scope of the present invention.

Example 1

After recovering liquid sap from fresh *Kappaphycus*, the residual granules are washed and dried. The known weight of dry granules was saccharified with dilute sulfuric acid at elevated temperature for specified period. Total sugar and reducing sugars are measured in the hydrolysate by phenol-sulfuric acid method and Nelson's method respectively. The conditions used for saccharification and sugar generated during saccharification are detailed in Table 1 & 2.

TABLE 1

| Carrageenan granules (g) | Sulfuric acid (%)/vol | Temperature (° C.) and time | Total Sugar (%) | Reducing sugar (%) |
|---|---|---|---|---|
| 10 | 0.3/200 ml | 121° C./15 min | 2.51 | 1.02 |
|  | 0.5/200 ml | 121° C./15 min | 2.96 | 1.21 |
|  | 0.7/200 ml | 121° C./15 min | 3.34 | 1.37 |
| 10 | 0.7/200 ml | 121° C./5 min | 2.33 | 0.95 |
|  |  | 121° C./10 min | 2.94 | 1.20 |
|  |  | 121° C./15 min | 3.28 | 1.34 |
| 10 | 0.7/200 ml | 37° C./1 day | 1.32 | 0.31 |
|  |  | 37° C./2 days | 1.42 | 0.58 |
|  |  | 60° C./1 day | 2.66 | 1.09 |
|  |  | 60° C./2 days | 3.38 | 1.38 |
| 10 | 0.5/200 ml | 100° C./1 h | 2.12 | 0.61 |

TABLE 2

| Carrageenan granules (g) | Sulfuric acid (%)/vol | Temperature (° C.)/time | Reducing sugar (%) |
|---|---|---|---|
| 3 | 0.5/100 ml | 80/1 h | 0.55 |
| 3 | 1.0/100 ml | 80/1 h | 0.52 |
| 3 | 2.0/100 ml | 80/1 h | 0.55 |
| 3 | 0.5/100 ml | 100/1 h | 0.73 |
| 3 | 1.0/100 ml | 100/1 h | 0.68 |
| 3 | 2.0/100 ml | 100/1 h | 0.76 |
| 3 | 0.5/100 ml | 100/2 h | 0.81 |

As described in Example 1, lower concentration of acid and one time extraction of carrageenan rich raw material yielded low concentration of sugar in the hydrolysate. To achieve high sugar concentration in the hydrolysate, repeated extraction with fresh raw material is done as described in Example 2

Example 2

To achieve maximum reducing sugar concentration in the hydrolysate, 20 g of washed and dried *Kappaphycus alvarezii* granules are extracted in 1000 ml of 0.5% sulfuric acid. The hydrolysate is flittered and same amount of new, fresh granule is added to the filtrate of earlier cycle and hydrolysed under similar conditions. Similarly, the cycles are repeated thrice. The sugar concentration obtained during each cycle is given in Table 3.

TABLE 3

| Cycle No. | Wt of granules (g) | Volume of acid/hydrolysate and strength | Time (h)/ temperature (° C.) | Vol (ml) of recovered hydrolysate | Reducing sugar (%) |
|---|---|---|---|---|---|
| 1 | 20 | 1000 ml/0.5% | 1/100 | 925 | 0.403 |
| 2 | 20 | 925 ml | 1/100 | 875 | 0.910 |
| 3 | 20 | 875 ml | 1/100 | 840 | 1.6 |

Here 13.44 g of total reducing sugar is recovered out of 60 g of granules which is equivalent to 48 g of carrageenan (after removal of moisture and fiber content (20%). Thus 28% of carrageenan is converted to simple sugar.

To increase the efficiency of hydrolysis and sugar concentration, higher acid concentration and repeated extraction was used which yielded better conversion of polysaccharide to simple sugars as described in Example 3.

Example 3

To achieve maximum reducing sugar concentration in the hydrolysate, 50 g of fresh granules is extracted in 1000 ml of 2.5% sulfuric acid and fresh granules is added to the filtrate of earlier cycle and hydrolysed under similar conditions. Similarly, the cycles are repeated thrice. The sugar concentration obtained during each cycle is given in Table 4.

TABLE 4

| Cycle No. | Wt of granules (g) | Volume of acid/hydrolysate and strength | Time (h)/ temperature (° C.) | Vol (ml) of recovered hydrolysate | Reducing sugar (%) |
|---|---|---|---|---|---|
| 1 | 50 | 1000 ml/2.5% | 1/100 | 975 | 1.5 |
| 2 | 50 | 975 ml | 1/100 | 900 | 3.3 |
| 3 | 50 | 900 ml | 1/100 | 850 | 5.2 |

Here 44.2 g of total reducing sugar is recovered out of 150 g of granules which is equivalent to 120 g of carrageenan (after removal of moisture and fiber content (20%). Thus 36.8% of carrageenan is converted to simple sugar.

Example 4

The saccharified solution obtained after acid hydrolysis of *Kappaphycus alvarezii* granules is acidic in nature, the pH of which is adjusted to 5.5-6.5 with solid calcium hydroxide. The resultant precipitates are removed by filtration and filtrate is used for fermentation after enriching it with 0.5% peptone and 0.5% yeast extract, autoclaving it and inoculating it with baker's yeast, purchased from local market and purified on glucose yeast extract agar. The inoculated broths (Broth 1 & broth 2), having different initial sugar concentration are incubated on shaker for 24 h to provide, initially, aerobic condition to the culture and then incubated further under anaerobic and static condition for the next two days. Ethanol formation is measured after every 24 h using GC-MS. Also, utilization of galactose is confirmed using HPLC where disappearance of galactose peak in the fermented broth is deduced with time of incubation. Conversion of reducing sugar, obtained from *Kappaphycus alvarezii* granules, into ethanol is explained in Table 5. Standard ethanol (0.1%) is used as reference for quantitative measurement. As shown in the Table 5, only 17-23% of the initial sugar is converted to ethanol

TABLE 5

| Sample | Initial Sugar conc in broth (%) (A) | Theoretical ethanol production (%) | Actual ethanol production (%) in broth | % conversion based on (A) |
|---|---|---|---|---|
| Broth-1 | 0.5 | 0.25 | 0.056 | 22.4 |
| Broth-2 | 1.6 | 0.8 | 0.14 | 17.4 |

Example 5

The saccharified solution obtained after acid hydrolysis of *Kappaphycus alvarezii* granules, having different initial sugar concentration, is acidic in nature, the pH of which is adjusted to 5.5-6.5 with solid calcium hydroxide. The resultant precipitates are removed by centrifugation or filtration and filtrate is used for fermentation after enriching it with 0.5% peptone and 0.5% yeast extract, autoclaving it and inoculating it with baker's yeast. The inoculated broth is incubated on shaker for 24 h to provide, initially, aerobic condition to the culture and then incubated further under anaerobic and static condition for next two days. Ethanol formation and reducing sugar utilization is measured after every 24 h using GC-MS and Nelson's method respectively. Conversion of reducing sugar into ethanol is presented in Table 6.

TABLE 6

| Sample | Initial Sugar conc in broth (%) (A) | Theoretical ethanol production (%) | Sugar utilized (%) (B) | Ethanol concn (%) in broth | % conversion based on (A) | % conversion Based on (B) |
|---|---|---|---|---|---|---|
| Fermentation broth-1 | 2.3 | 1.15 | 0.96 | 0.184 | 16.0 | 38.0 |
| Fermentation broth-2 | 2.82 | 1.41 | 1.1 | 0.1812 | 12.9 | 32.9 |

Here, only 32-38% of the sugar utilized is converted to ethanol as many other products are also produced along with ethanol like butanol, methyl butanol, iso butanol, ethyl acetate, propionic acid ethyl ester etc. which are reported as by-products during fermentation of sugars.

Bakers yeast, used for the experiment might not be suitable for ethanol fermentation and hence two standard yeast cultures of *Saccharomyces cerevisiae* were procured from NCIM, NCL, Pune and experiments were conducted using them to identify the promising one which is described in Example 6.

Example 6

The saccharified solution obtained after acid hydrolysis of *Kappaphycus alvarezii* granules, having different initial sugar concentration where pH is adjusted to 5.5-6.5 with solid calcium hydroxide. The clear solution obtained after removal of precipitates is used for fermentation after enriching it with nitrogen sources like 0.5% peptone and 0.5% yeast extract, autoclaving it and inoculating it with two standard yeast cultures of. *Saccharomyces cerevisiae* culture No. NCIM 3455 (ATCC 26602) and NCIM 3090 (ATCC 9763) obtained from NCL, Pune, India. The inoculated broth is incubated on shaker for 24 h to provide, initially, aerobic condition to the culture and then incubated further under anaerobic and static condition for next three days. Ethanol formation is measured after four days using GC-MS along with measurement of unutilized sugar. Conversion of reducing sugar into ethanol is indicated in Table 7.

TABLE 7

| Time | NCIM 3455 | | | | NCIM 3090 | | |
|---|---|---|---|---|---|---|---|
| | Initial sugar conc (%) | Sugar utilized (%) | Ethanol conc (%) | % ethanol conversion based on sugar utilized | Sugar utilized (%) | Ethanol conc (%) | % conversion based on sugar utilized. |
| 96 hours | 2.3 | 1.33 | 0.35 | 52.6 | 0.420 | 0.049 | 23.3 |

Here, strain NCIM 3455 is found to be superior with respect to ethanol formation.

Example 7

Bioethanol production using *Kappaphycus alvarezii* granules is conducted as under. 50 g of biomass is hydrolyzed with 1000 ml of 2.5% sulfuric acid at 100° C. for one hour. The extract is filtered and 50 g of fresh seaweed biomass is added to the filtrate and hydrolysis is repeated under similar condition to increase the sugar concentration. Thus, extraction is repeated thrice using total 150 g of raw material. Reducing sugar concentration is measured in the extracts of all the three cycles (Table 8). The saccharified solutions obtained after three cycles is neutralized to pH 5.5-6.0 with solid calcium hydroxide. The clear solution obtained after removal of calcium sulfate precipitates is used for fermentation after enriching it with nitrogen sources like 0.5% peptone and 0.5% yeast extract, autoclaving it and inoculating it with the promising standard yeast cultures of *Saccharomyces cerevisiae* culture No. NCIM 3455 (ATCC 26602). The inoculated broth is incubated on shaker for 24 h to provide, initially, aerobic condition to the culture and then incubated further under anaerobic condition on shaker for next two days. Ethanol formation is measured after every 24 h using GC-MS along with measurement of unutilized sugar. Conversion of reducing sugar into ethanol is explained in Table 9. The results indicate that most of the sugar utilized is converted into ethanol.

After three cycles, 36.82 g of reducing sugar is obtained from 150 g granules which are equivalent to 120 g of carrageenan. Thus 30% of carrageenan is converted in to reducing sugar.

TABLE 8

Sugar concentration of extracts of *Kappaphycus alvarezii* granules

| Cycle No | Weight of *Kappaphycus alvarezii* granules | Volume of Resultant extract (ml) | Sugar concentration (%) |
|---|---|---|---|
| 1 | 50 | 875 | 1.86 |
| 2 | 50 | 740 | 3.26 |
| 3 | 50 | 620 | 5.94 |

TABLE 9

Sugar utilization and ethanol formation using *Kappaphycus alvarezii* granules

| | *Kappaphycus alvarezii* | | | |
|---|---|---|---|---|
| Day of fermentation | Sugar in hydrolysate (%) | Sugar utilized (%) (A) | Ethanol production (%) | % conversion based on (A) |
| 0 | 5.94 | — | — | — |
| 1 | 4.4 | 1.54 | 0.99 | 100 |

TABLE 9-continued

Sugar utilization and ethanol formation using *Kappaphycus alvarezii* granules

| | *Kappaphycus alvarezii* | | | |
|---|---|---|---|---|
| Day of fermentation | Sugar in hydrolysate (%) | Sugar utilized (%) (A) | Ethanol production (%) | % conversion based on (A) |
| 2 | 4.2 | 1.74 | 0.89 | 92.78 |
| 3 | 4.0 | 1.94 | 0.90 | 83.92 |

Here, most of the sugar utilized is converted into ethanol. However, efficiency of sugar utilization is very slow which was due to the presence of soluble salts in the hydrolysate, interfering the fermentation efficiency of the culture. To overcome this issue, electrodialysis process was used to reduce the soluble salt content in the hydrolysate.

Example 8

Bioethanol production using *Kappaphycus alvarezii* granules is conducted as under. 50 g of biomass is hydrolyzed with 1000 ml of 2.5% sulfuric acid at 100° C. for one hour. The extract is filtered and 50 g of fresh seaweed biomass is added to the filtrate and hydrolysis is repeated under similar condition to increase the sugar concentration. Thus, extraction is repeated five times using total 250 g of raw material. Reducing sugar concentration is measured in the final hydrolysate. The saccharified solutions obtained after five cycles is neutralized to pH 5.5-6.5 with solid calcium hydroxide. Insoluble salts generated during the process of neutralization is removed by filtration or centrifugation at 6500 rpm for 15 mins whereas soluble salts generated during the process of hydrolysis and neutralization is removed by electrodialysis (ED) method. An electrodialysis stack was packed with 5 cell pairs of cation and anion exchange membranes of inter polymer type prepared in this laboratory. A parallel flow was employed in the stack. The single effective membrane area of the stack was 80 cm$^2$. The seaweed hydrolysate was circulated through the product (diluate) compartments of the ED stack. At the same time water was circulated through the concentrate compartments. All the experiments were carried out at circulation flow rate of 3.0 L/h each for product and concentrate streams by using suitable pumps. A dilute solution of sodium sulfate was circulated through the two electrode compartments at the end to remove the products of electrodialysis. Electrical potential (7.5 V) was applied between the two electrodes by means of an AC-DC rectifier. The circulation of both, diluate and concentrate streams were continued till the total dissolved salt rejection reaches about 90-95% of the initial quantity. At regular intervals current, voltage and TDS were recorded. At the end of the experiment, test samples of diluate and concentrate streams were analyzed for TDS, conductivity, pH, chloride, sulfate, hardness, sodium, potassium etc. The clear solution obtained after ED is used for fermentation after enriching it with nitrogen sources like 0.5% peptone and 0.5% yeast extract, autoclaving it and inoculating it with the promising standard yeast cultures of *Saccharomyces cerevisiae* culture No. NCIM 3455 (ATCC 26602). The inoculated broth is incubated at 30±2° C. on shaker for 24 h and ethanol formation is measured using GC-MS along with measurement of unutilized sugar. Effect of electrodialysis on ethanol production is studied by comparing it with the results obtained with the same hydrolysate without ED. Analysis of ED treated hydrolysate is presented in Table 10 whereas comparative data on ethanol production from ED treated and ED untreated hydrolysate is presented in Table 11.

TABLE 10

Analysis of ED treated hydrolysate prepared from *Kappaphycus alvarezii* granules

| Sample | Volume (ml) | TDS (ppm) | Sugar (%) | Conductivity (mS) | Chloride (g/l) | pH |
|---|---|---|---|---|---|---|
| ED treated hydrolysate | 440 | 3800 | 8.6 | 6.3 | 0.38 | 6.72 |
| Reject 1 | 500 | 31000 | 3.5 | 40.3 | 7.36 | 8.65 |
| Reject 2 | 550 | 6000 | 0.18 | 10.3 | 1.20 | 8.18 |

TABLE 11

Effect of ED on production of ethanol from *Kappaphycus alvarezii*:

| Sample | Initial sugar (%) | Remaining sugar in fermented broth (%) | Sugar utilized (%) | Theoretical EtOH prodn (%) | Actual EtOH prodn (%) | Conversion efficiency (%) |
|---|---|---|---|---|---|---|
| Without ED | 8.8 | 6.2 | 2.8 | 1.4 | 0.175 | 12.5 |
| ED treated | 8.6 | 4.1 | 4.5 | 2.25 | 2.05 | 87.8 |

Due to high sulfate content of carrageenan, the repeated processes of acid hydrolysis and neutralization resulted in the generation of high concentration of soluble salts which interfered with the fermentation process. Removal of soluble salts up to 90% using electrodialysis is process significantly improved utilization of sugar and its conversion to ethanol.

Example 9

The saccharified solution obtained after acid hydrolysis of *Kappaphycus alvarezii* granules, having different initial sugar concentration where pH is adjusted to 5.8 with solid calcium hydroxide. The clear solution obtained after removal of precipitates through filtration or centrifugation at 7000 rpm for 15 min. is subjected to electrodialysis for desalting and then used for fermentation after enriching it with nitrogen source like protein hydrolysate prepared from *Jatropha* cake having 1.25% protein, instead of 0.5% peptone and 0.5% yeast extract, autoclaving it and inoculating it with standard yeast cultures of *Saccharomyces cerevisiae* NCIM 3455 (ATCC 26602). The inoculated broth is incubated at 30±2° C. on shaker for 24 h to provide, initially, under aerobic condition to the culture and then incubated further under anaerobic and static condition for next three days. Ethanol formation is measured after four days using GC-MS along with measurement of unutilized sugar. After incubation, sugar utilization was as high as 84% of total sugar available in the hydrolysate however, percentage conversion of sugar to ethanol was as low as 13.5%.

ADVANTAGES OF THE PRESENT INVENTION 1. exploitation of macroalgal biomass for ethanol production integrated with biofertilizer production where ethanol is generated as a byproduct.
2. after carrageenan production, surplus carrgaeenan rich granules are used as a source of sugar, for ethanol production
3. obtaining multiple products from the same seaweed makes its commercial cultivation economically more viable
4. vast area is available in the Sea for commercial cultivation of potential seaweeds.
5. no competition for agricultural land and water and with food crops.
6. no precise agricultural practices required for seaweed cultivation
7. no use of fertilizer or pesticides and hence eco-friendly cultivation method.
8. use of electrodialysis process form removal of soluble salts present in the hydrolysate
9. use of waste products, generated during neutralization and electrodialysis and after distillation of ethanol, as manure.

We claim:
1. A process for integrated production of ethanol and seaweed sap from *Kappaphycus alvarezii* comprising the steps of:
   (a) hydrolyzing washed carrageenan rich *Kappaphycus alvarezii* granules, obtained after extraction of salt from *Kappaphycus alvarezii*, using dilute sulfuric acid in the range of 0.5-5%, followed by heating the solution in the range of 80-120° C. for a period in the range of 30-90 minutes to obtain a reducing sugar rich hydrolysate;
   (b) recovering the sugar rich hydrolysate as obtained in step (a) by filtration or centrifugation in the range of 5000-7000-rpm for 15 minutes to obtain a filtered or centrifuged solution;
   (c) increasing a reducing sugar concentration in the sugar rich hydrolysate as obtained in step (b) by adding fresh *Kappaphycus alvarezii* granules to the filtered or centrifuged solution followed by repeating the steps (a) and (b) until the reducing sugar concentration is attained in the range of 2 to 10%;
   (d) adjusting the pH of the sugar rich hydrolysate as obtained in step (c) in the range of 4.5 to 8.0 using alkali comprising calcium to generate insoluble $CaSO_4$;
   (e) separating insoluble $CaSO_4$ as obtained in step d) by filtration or centrifugation in the range of 5000-7000 rpm to obtain a filtered or centrifuged hydrolysate;

(f) desalting the filtered or centrifuged hydrolysate as obtained in step (e), to remove soluble salts, by electrodialysis;

(g) enriching the desalted hydrolysate as obtained in step (f) with a nitrogen source in the range of 0.2-2.0% followed by sterilization at 121° C. for 15 minutes to produce an enriched and sterilized hydrolysate;

(h) inoculating the enriched and sterilized hydrolysate as obtained in step (g) with a yeast culture of *Saccharomyces* and incubating in the range of 25-35° C. for a period in the range of 24 to 96 hours to obtain ethanol;

(i) separating ethanol as obtained in step (h) from fermented broth by distillation; and (j) concentrating ethanol as obtained in step (i) by distillation to obtain concentrated ethanol.

2. The process of claim 1, wherein the reducing sugar concentration of the hydrolysate as obtained in step (c) is increased from 2.0% to 10% by repeated hydrolysis of fresh *Kappaphycus alvarezii* granules in the same solution.

3. The process of claim 1, wherein the yeast culture of step (h) is *Saccharomyces cerevisiae*.

4. The process of claim 1 or 3, wherein said enriched and sterilized hydrolysate is incubated under aerobic or anaerobic conditions for fermentation of sugar to ethanol.

5. The process of claim 1, wherein the fermented broth remaining after distillation in step (i) and insoluble $CaSO_4$ remaining after filtration or centrifugation in step (e) are used as manure.

* * * * *